(12) United States Patent
Radman et al.

(10) Patent No.: US 9,193,974 B2
(45) Date of Patent: Nov. 24, 2015

(54) PROCESS FOR CHROMOSOMAL ENGINEERING USING A NOVEL DNA REPAIR SYSTEM

(75) Inventors: Miroslav Radman, Paris (FR); Ksenija Zahradka, Paris (FR)

(73) Assignee: DEINOVE, Grabels (FR)

( * ) Notice: Subject to any disclaimer, the term of this patent is extended or adjusted under 35 U.S.C. 154(b) by 1258 days.

(21) Appl. No.: 12/227,171

(22) PCT Filed: May 10, 2006

(86) PCT No.: PCT/EP2006/005826
§ 371 (c)(1), (2), (4) Date: Apr. 23, 2009

(87) PCT Pub. No.: WO2007/128338
PCT Pub. Date: Nov. 15, 2007

(65) Prior Publication Data
US 2009/0227029 A1     Sep. 10, 2009

(51) Int. Cl.
*C12N 15/74* (2006.01)

(52) U.S. Cl.
CPC ..................................... *C12N 15/74* (2013.01)

(58) Field of Classification Search
None
See application file for complete search history.

(56) References Cited

FOREIGN PATENT DOCUMENTS

WO    01/64951    9/2001

OTHER PUBLICATIONS

Cox Michael M. et al., "Deinococcus Radiodurans—The Consummate Survivor", Nature Reviews Microbiology, vol. 3, No. 11, Nov. 2005, pp. 882-892, XP002415708.
Englander Joseph et al., "DNA Toroids: Framework for DNA Repair in Deinococcus Radiodurans and in Germinating Bacterial Spores", Journal of Bacteriology, vol. 186, No. 18, Sep. 2004, pp. 5973-5977, XP002415709.
Levin-Zaidman Smadar et al., "Ringlike Structure of the Deinococcus Radiodurans Genome: A key to Radioresistance?", Science, vol. 299, No. 5604, Jan. 10, 2003, pp. 254-256, XP002415710.
Wilson Thomas E. et al., "Non-homologous end-Joining: Bacteria Join the Chromosome Breakdance", Trends in Biochemical Sciences, vol. 28, No. 2, Feb. 2003, pp. 62-65, XP002415711.
International Search Report for PCT/EP2006/005826, mailed Feb. 6, 2007.

*Primary Examiner* — Nancy T Vogel
(74) *Attorney, Agent, or Firm* — Nixon & Vanderhye P.C.

(57) ABSTRACT

This invention relates to chromosomal engineering via DNA repair process. The process of the invention comprises the steps of: 1) submitting at least one source of biological activity, e.g. *Deinococcus radiodurans*, to radiation, desiccation and/or chemical treatment liable to damage the DNA, so as to substantially shatter its chromosomes into short fragments; 2) annealing complementary single strand tails extended by the synthesis templated on partially overlapping DNA fragments of said shattered chromosomes; 4) converting the resulting long linear DNA intermediates into intact circular chromosomes, by means of a RecA dependent homologous recombination; whereas at least one foreign source of genetic material, e.g. DNA, can be introduced during steps 2 and/or 3; and 4) optionally separating and collecting the recombined chromosomes thus obtained.

11 Claims, 5 Drawing Sheets

FIG 1: Kinetics of DNA repair and Rate of DNA synthesis

FIG 2: Density gradient analysis of DNA repaired after gamma irradiation in the presence of heavy anolog 5-BrdU Open symbols: non-irradiated culture; red, closed symbols: irradiated, 3 h repair.
A1-A3: pre-labelled DNA; B1-B3: post-labelled DNA; C1-C3: pre & post-labelled.
A-C: neutral CsCl gradients; A1-C1: alkaline gradients; A2-C2: sonicated DNA, neutral gradients.

FIG3: THE STRUCTURE OF REPAIRED CHROMOSOMES

Repair synthesis in γ-irradiated *D. radiodurans* revealed by photolysis of 5-BrdU substituted DNA Lane 1: *S. cerevisiae* standard (225 – 2200 kbp)
Lanes 2-7: *D radiodurans thy⁻* DNA
    2: unirradiated, time 0
    3: 7 kGy irradiated, time 0
    4: 3 h postirradiation
    5: 3 h postirradiation, + UV (1000 J/m$^2$)
    6: 3 h postirradiation + BUdR
    7: 3 h postirradiation + BUdR, + UV (1000 J/m$^2$)

FIG 4: SSA vs SDSA mechanisms for repairing *D. radiodurans* DNA shattered by ionizing radiation

FIG 5

FROM 100 FRAGMENTS TO THE REPAIRED CHROMOSOME:
Involvement of two mechanisms of DNA recombination repair in *D. radiodurans*

PROCESS FOR CHROMOSOMAL ENGINEERING USING A NOVEL DNA REPAIR SYSTEM

This application is the U.S. national phase of International Application No. PCT/EP2006/005826, filed 10 May 2006 which designated the U.S., the entire contents of which are hereby incorporated by reference.

FIELD OF THE INVENTION

This invention relates to a chromosomal engineering process and to its use, especially for producing large repertoires of inter-species genomic mosaics encoding a wide variety of metabolic pathways.

BACKGROUND OF THE INVENTION

Hundreds of partially overlapping chromosomal fragments could be conceivably rejoined via mechanisms involving no significant DNA synthesis, e.g., by (i) non-homologous end-joining (NHEJ) of DNA fragments[1,2] held in register by some special form of chromatin[3] or (ii) homologous recombination (HR) via conservative crossovers involving ends of overlapping fragments[4-6]. Because of the large number of DNA fragments, significant DNA repair synthesis can be involved in (iii) single-strand annealing (SSA) requiring a strand-biased exonucleolytic erosion of the DNA fragments' ends liberating the complementary strands for the annealing with other fragments' complementary single-strand protrusions[4]. Alternatively, fragment assembly could require or involve massive DNA synthesis, e.g., (iv) by strand invasion between overlapping fragments (D-loop formation) priming the extension of paired 3' ends (e.g., by a moving D-loop, like in transcription, FIG. 4) to the end of the templating fragment, followed by the annealing of thus extended ends via complementary single-strand tails (so-called synthesis dependent strand annealing or SDSA mechanism[7]), or (v) by any kind of "copy-choice" (CC) DNA replication mechanism switching between and copying double-stranded templates from one fragment to another until a full-size chromosome is newly synthesised[8].

It is an object of the present invention to form novel hybrid species or novel chromosomes by in vivo intergeneric and/or interspecific recombinations, in a way that is both efficient and easy to reduce to practice.

It is another object of this invention to use in vivo chromosomal engineering, e.g. in an extremophile bacterium *Deinococcus D. radiodurans*, or any other radiation and/or desiccation and/or chemical treatment resistant organism possessing similar DNA repair mechanisms (the herein described ESDSA) for assembling their fragmented DNA into intact functional chromosomes.

It is still another object of this invention to use in vitro chromosomal engineering, e.g. in *D. radiodurans* cell-free extracts, or in active cell-free extracts of any other radiation and/or desiccation resistant organism possessing similar DNA repair mechanisms (the herein described ESDSA) for assembling their fragmented DNA into intact functional chromosomes. It is another object of this invention to use the aforesaid strategy to provide sites of integration of exogenous DNA by adding single-stranded or double-stranded terminal additions identical, or similar to, any chromosomal sequence as sites for their integration during the DNA repair process either in vivo or in vitro.

It is another object of this invention to use intact or fragmented DNA from any biological species, or even DNA created by artificial synthesis, as genetic elements to be integrated into the bacterial chromosome and become an integral part thereof.

Still another object of this invention is to use intact or fragmented DNA from any biological species, or even DNA created by artificial synthesis, as genetic elements to be integrated into artificial chromosomes by either in vivo or in vitro chromosomal assembly processes.

It is another object of this invention to use natural transformation capacity, or bacterial sex (e.g., conjugation or transduction), or artificial means (electroporation or chemical modification of the cellular membrane) of introducing foreign DNA into the target cells undergoing DNA repair. This ongoing repair by fragment assembly is triggered by ionizing or ultraviolet irradiation, or by chemicals that damage DNA (e.g., mitomycin C) before or after the introduction of foreign DNA in the bacterial cell. It is another object of this invention to use large genomic or plasmidic DNA fragments containing entire operons for biosynthetic pathways producing (i) useful small molecules or therapeutic proteins, (ii) enzymatic activities for biodegradation or bioremediation of the environment or (iii) energy generating metabolism, for example taking also advantage of the extreme desiccation resistance of *D. radiodurans* and its innocuousness for humans.

It is still another object of this invention to use a source of biological activity according to this invention as the vector for natural or engineered biodegradation and bioremediation pathways.

It is still another object of this invention to use this chromosomal engineering process in cell free extracts, or with purified proteins, for generating new chromosomal assemblies that can be transferred into appropriate cells, or DNA-free cells, creating new biological entities. These new biological entities or species can be used as biological machines tailored to solve major problems for humanity, e.g., environmental clean-up through biodegradation, synthesis of new therapeutics, clean energy production etc.

SUMMARY OF THE INVENTION

This invention is based on a combination approach by which chromosomal engineering of a source of biological activity and optionally of an exogenous source of genetic material to be recombined, becomes feasible on the basis of a newly discovered form of DNA repair, involving mutually dependent DNA replication and recombination processes, one of which involves special "extended synthesis dependent strand annealing" (ESDSA) for reconstituting functional chromosomes previously shattered by radiation or extensive desiccation, whereas the other one makes use of homologous recombination.

The source of biological activity used according to the invention is advantageously selected from the group consisting of:
(a) a bacterium resistant to ionizing radiation and/or desiccation and/or chemical treatment, and showing a repair pathway, after radiation and/or desiccation and/or chemical treatment, said repair pathway involving both ESDSA and homologous recombination processes;
(b) any living organism with a similar DNA repair pathway; and
(c) cell-free extracts of a bacterium according to (a) or of a living organism according to (b) above, prepared at the peak cellular DNA repair activity.

An exemplary source of biological activity according to the invention is the bacterium *Deinococcus radiodurans*, which is a well known small non-sporulating and non-pathogenic bacterium.

According to this invention, an exogenous source of genetic material can be selected from the group consisting of, e.g., DNAs of various nature and/or origin and even any genetic material of the biosphere.

The chromosomal engineering process according to this invention can be used, among others, for reassembling fragmented DNA into intact functional chromosomes, for in vivo or in vitro integrating exogenous DNA during a DNA repair process, for integrating genetic elements into a bacterial chromosome or into artificial chromosomes, for natural or engineered biodegradation and/or bioremediation, for synthesis of new compounds etc.

BRIEF DESCRIPTION OF THE DRAWINGS

FIG. 1 is a representation of DNA repair and synthesis following gamma irradiation of *D. radiodurans*. A, C, E show the kinetics of DNA repair in wild type, polA and recA strains respectively. B, D, F show, on the log scale, the respective rates of DNA synthesis. A: (c) line shows the PFGE Not1 restriction patterns of DNA from non-irradiated wild type cells, (o) immediately after 7 kGy gamma irradiation (DNA fragments are about 25-30 kb) and from the irradiated cells grown in rich medium for 1.5, 3 and 4.5 h. (s) shows the *S. cerevisiae* chromosomes as molecular markers. B: incorporation of radioactive 3H-thymidine during 15 min pulse labelling measures the global rate of DNA synthesis in irradiated (red line) and non-irradiated (black line) cultures. C: the same experiment as in A for the polA mutant. D: the same experiment as in B for the polA mutant, E: the same as in A and C for the recA mutant. F: the same as in B and D for the recA mutant.

FIG. 2 is a representation of an analysis of repaired *D. radiodurans* DNA by the 5-BrdU density labelling. *D. radiodurans* thy-cells were radioactively and density labeled by the growth in the presence of 3H-thymidine and 5-BrdU respectively. Genomic DNA was extracted and analyzed by CsCl density centrifugation. HH, HL and LL refer to double-stranded heavy/heavy, heavy/light and light/light molecules. H and L refer to single-stranded heavy and light molecules. A, A1, A2: <<pre-labeled>> DNA (labeled before irradiation); B, B1, B2: <<post-labeled>>DNA (labeled after irradiation); C, C1, C2: <(pre- and post-labeled>> DNA. A, B, C: native DNA in neutral CsCl gradients; A1, B1, C1: denatured DNA in alkaline CsCl gradients; A2, B2, C2: sonicated DNA in neutral gradients. Black open circles: DNA density profiles of non-irradiated cultures grown for 2.5 hours (one mass-doubling) in 5-BrdU-supplemented medium; red closed circles: same for 7 kGy-irradiated cells grown for 3 hours in 5-BrdU-supplemented medium.

FIG. 4 is a representation of models for the assembly of small chromosomal fragments into long linear intermediates respectively by Single Strand Annealing (SSA) and Extended Synthesis. Dependent Strand Annealing (ESDSA) recombination processes. Up to 10 genomic copies of exponentially growing *D. radiodurans* cells are each randomly broken into about 100 fragments. Following 5' to 3' end recession (1) diffused fragments can rejoin directly via annealing of complementary single stranded overhangs of overlapping fragments (step 4, SSA pathway): the gaps are repaired by synthesis and any strand excess trimmed by nucleases (5). In the ESDSA pathway, the end-recessed fragments (1) prime synthesis templated on the intact parts of other partially overlapping fragments (2), presumably via a moving D-loop shown in the bracketed intermediate. The strand extension can run to the end of the template producing fragments with 3' single strand extended by de novo synthesis (3). All fragments can interact under the constraints of single-stranded homology. The extended single strands can a priori engage in multiple rounds of extension (like in single round multiplex PCR with a growing primer) until their extended ends find a complementary partner for SSA (4); these linear intermediates are trimmed and/or gap-filled and finally ligated (5). The de novo strand extension synthesis is shown by widened lines. Hydrogen bonds are indicated only for inter-fragment associations. All data support the ESDSA pathway for producing long linear DNA.

GENERAL DESCRIPTION OF THE INVENTION

It has now been discovered that a novel kind of chromosomal engineering can be carried out in vivo or in vitro with *D. radiodurans* and/or possibly with other radiation-, desiccation- and/or chemical treatment-resistant organisms) as the source of biological activity, provided that the said source of biological activity is able to accomplish or to be induced to accomplish a fragmented DNA-repair mechanism for assembling the fragmented DNA into intact functional chromosomes, preferably together with exogenous genetic elements to be integrated into the bacterial chromosome and become an integral part thereof.

The inventors, in order to discriminate between different hypothetical mechanisms listed in the section "Background of the Invention" hereinabove, have explored in parallel the kinetics of the joining of DNA fragments by pulsed-field gel electrophoresis (PFGE) and the rate of DNA synthesis by 15 min $^3$H-TdR pulse labelling following 7 kGy gamma radiation.

Figure 1:
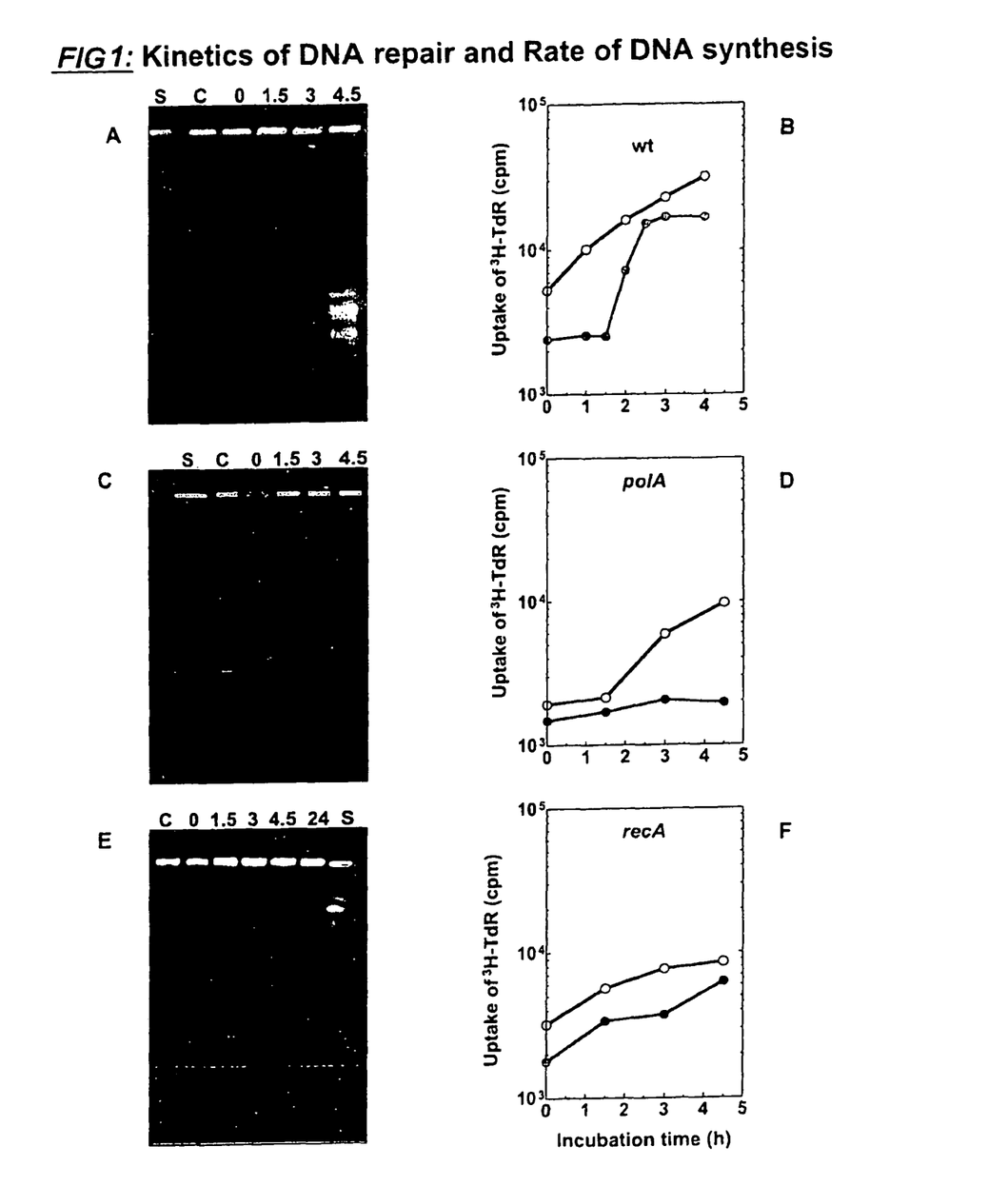

It has thus been revealed that there is a temporal coincidence of the fragment assembly and the observed massive DNA synthesis occurring without cell division at much higher rate than in the growing non-irradiated cell culture (FIGS. 1A and B). This DNA synthesis is absent in a polA strain (FIG. 1D) that also shows no evidence of DNA repair (FIG. 1C). Along with high radiation and/or desiccation sensitivity of the polA mutant, these observations cannot be easily accommodated by mechanisms (i) and (ii). They generally agree with all mechanisms (iii-v) involving extensive DNA synthesis. ESDSA (iv), and to a lesser degree SSA (iii) mechanisms are favored if the PolA dependence is due to PolA (with or without participation of DNA pol III) catalyzed single-strand elongation (FIG. 4), but the CC mechanism (v) cannot be a priori excluded because PolA could initiate or otherwise facilitate a Pol III-catalyzed semi-conservative two-strand synthesis (replication forks).

The inventors have now shown that a most efficient and precise known DNA repair pathway is afforded when the DNA repair involves "extended synthesis dependent strand annealing" ESDSA) and homologous recombination processes, and that such a DNA repair pathway can be used for the production of large repertoires of inter-species genomic mosaics encoding a wide variety of metabolic pathways. The source of biological activity providing the activity for chromosomal engineering according to the invention should be resistant to ionizing radiation and desiccation, which shatter its genome into of short DNA fragments subsequently reassembled into functional chromosomes.

The ESDSA step requires DNA polymerase I presumably for the extensive elongation of fragments' single-stranded ends facilitating their annealing, whereas the ESDSA-generated long linear intermediates thus obtained are matured in the further step by homologous recombination into circular chromosomes that are patchworks of "old" (i.e. synthesized before radiation and/or desiccation) and "new" (i.e. synthesized after radiation and/or desiccation) DNA blocks.

More specifically, the inventors have thus shown that such an efficient and precise mechanism is afforded by radiation-, chemical treatment- and/or desiccation-resistant bacteria, e.g. by the radiation resistant *Deinococcus radiodurans* bacterium, or by any other equivalent source of biological activity or cell-free extracts of source of biological activity possessing similar DNA repair mechanisms for reassembling their fragmented DNA.

In a first aspect, the invention provides a process for the reconstitution or recomposition of chromosomes shattered by radiation, chemical treatment and/or desiccation, wherein the process comprises the steps of:
1) submitting at least one source of biological activity (e.g. *D. radiodurans*) to radiation, desiccation and/or chemical treatment, so as to substantially shatter its chromosomes into short fragments;
2) annealing complementary single strand tails extended by the synthesis templated on partially overlapping DNA fragments of said shattered chromosomes;
3) converting the resulting long linear DNA intermediates into intact circular chromosomes, by means of a RecA dependent homologous recombination; and
4) optionally separating and collecting the recombined chromosomes thus obtained.

This process can be carried out either in vivo or in vitro, depending on the type of the source or combination of sources of biological activity which is used.

This invention is based on a chromosomal engineering by means of a newly discovered form of DNA repair, involving mutually dependent DNA replication and recombination processes, one of which involves special "extended synthesis dependent strand annealing" (ESDSA) for reconstituting functional chromosomes previously shattered by radiation or extensive desiccation, whereas the other one makes use of homologous recombination.

In embodiments of the first aspect of the invention, the source of biological activity used according to the invention is advantageously selected from the group consisting of:
(a) a bacterium resistant to ionizing radiation and/or desiccation and/or chemical treatment, and showing a repair pathway, after radiation and/or desiccation and/or chemical treatment, involving both ESDSA and homologous recombination processes;
(b) any living organism with a similar DNA repair pathway; and
(c) cell-free extracts of a bacterium according to (a) or of a living organism according to (b) above.

This process can be carried out in vivo or in vitro.

In certain preferred embodiments of the first aspect of the invention, the process of the invention can be carried out in the bacterium *Deinococcus radiodurans*, or any organism with similar DNA repair pathway, or in cell-free extracts of bacterium *Deinococcus radiodurans*, or any organism with similar DNA repair pathway.

This process is based on mechanisms whereby the said at least one source of biological activity reconstitutes its genome from fragments produced by a procedure consisting of very high doses of ionizing radiation such as gamma or X rays, extensive desiccation, ultraviolet irradiation, or use of chemicals liable to damage DNA, such as mitomycin C.

The process involves as a step 2 an "extended synthesis dependent strand annealing", or ESDSA, the principal features of which are: (i) pairing of a single-stranded end of one fragment with the identical sequence on another, partially overlapping, fragment, (ii) extension of the paired end by the DNA synthesis, (iii) the extended newly synthesized ends from different fragments find in the cell another extended end that is complementary, i.e. shares the sequence homology, and anneal together to form a newly synthesized DNA duplex linking the two fragments.

The said process can be continued with other complementary ends, leading eventually to long intermediates which are patched-up together to form intact circular chromosomes by a homologous recombination process requiring the RecA or a similar protein.

In this process, steps 2 and 3 taken together represent a complete chromosomal DNA repair process.

In certain preferred embodiments of the first aspect of the invention, the at least one source of biological activity is exposed to at least one gamma irradiation less or more than 0.7 megarad (7 kGy), used in this study sufficient for fragmenting the chromosomes of the said source of biological activity.

As an alternative, the at least one source of biological activity can be exposed to a desiccation procedure, preferably during a period of time of about 2 months.

Most preferably, step 2) of the process of the invention comprises an extended synthesis-dependent strand annealing (ESDSA).

In a second aspect the invention provides a process which further comprises, for providing sites of integration of exogenous DNA into the chromosome or the at least one source of biological activity, the addition of single-stranded or double-stranded terminal sequences identical or similar to any chromosomal sequence as sites for their integration during the DNA repair process either in vivo or in vitro.

In a third aspect the invention further comprises the use of at least one source of genetic material, e.g. of at least one DNA selected from the group consisting of intact or fragmented DNA from any biological species or DNA created by artificial synthesis. Preferably, said source of genetic material or of genetic elements is integrated into the said shattered chromosomes so as to become an integral part thereof during steps 2) and/or 3) of the process according to this invention.

Most preferably, in embodiments of the third aspect of the invention, the process comprises the use of more than one DNA selected from the group consisting of intact or fragmented DNA from any biological species and DNA created by artificial synthesis.

In preferred embodiments of the third aspect of the invention, the bacterium *D. radiodurans* being naturally highly transformable by DNA, the at least one foreign DNA and/or DNA fragment is introduced into irradiated *D. radiodurans* cells during the process of DNA repair.

Most preferably the integration of the foreign DNA fragments into the genome of *D. radiodurans* are assured by the synthetic extensions of 3' ends of foreign DNA.

In order to assure successful integration in the bacterial chromosome, the foreign DNA is preferably extended by synthesis or end-addition by DNA ligase with a chosen bacterial sequence, e.g. corresponding to one of its IS sequences, to offer multiple choices of harmless integration.

In certain embodiments of the third aspect of the invention, after extensive chromosomal DNA breakage by ionizing radiation, desiccation and/or chemicals, the said 3' terminal sequence is used for the priming of DNA synthesis and strand extension on any of the IS sequences into its specific neighboring unique sequence during the course of DNA repair.

In a preferred embodiment of the third aspect of the invention, all of the DNA fragments from any chosen source of genetic material, or mixture of materials, is extended by the same sequence such that—in the same cell—these DNA fragments can be directly end-annealed, in any possible combination, before being integrated into the chromosome.

Any source of genomic chromosomal or extra-chromosomal (e.g. plasmidic) DNA can be used as the candidate for insertion into said shattered chromosome.

In certain embodiments of the third aspect of the invention, genes encoding entire biosynthetic pathways, e.g. for biodegradation of environmental pollutants, for bioconversion of energy, or for synthesis of antibiotics, therapeutic proteins or other useful compounds, can be used.

For an application to the synthesis of therapeutic proteins, also the genes for their post-synthetic modification can be integrated.

In a fourth aspect, the invention provides an artificial DNA prepared with the process according to this invention. Most preferably, said artificial DNA comprises large genomic chromosomal or non-chromosomal DNA fragments containing entire operons for biosynthetic pathways.

In a fifth aspect, the invention provides use such an artificial DNA for producing (i) useful small molecules or therapeutic proteins, (ii) enzymatic activities for biodegradation or bioremediation of the environment, or (iii) energy generating metabolism.

In certain embodiments of the fifth aspect of the invention, the artificial DNA thus prepared is to be used for producing large repertoires of inter-species genomic mosaics encoding a wide variety of metabolic pathways.

In another embodiment of the fifth aspect of the invention, the process is to be used in cell free extracts, or with purified proteins, for generating new chromosomal assemblies that can be transferred into appropriate cells, or DNA-free cells, creating new biological entities. Most preferably the said new biological entities are intended to be used as biological machines tailored to solve major problems for humanity, especially environmental clean-up through selective biodegradation, synthesis of new therapeutics and/or clean energy production.

In certain embodiments of all the aspects of the invention, the process further comprises the use of at least one means selected from the group consisting of natural transformation capacity, bacterial sex, such as conjugation or transduction capabilities, and artificial means, such as electroporation or chemical modification of the cellular membrane, for introducing foreign DNA into the living cells of at least one target source of biological activity undergoing DNA repair.

In preferred embodiments of all the aspects of the invention, the process further comprises triggering by ionizing or ultraviolet irradiation, or by chemicals that damage DNA, such as mitomycin C, before or after the introduction of foreign DNA into the said source of biological activity.

Most preferably, *D. radiodurans* is used as a vector for natural or engineered biodegradation and bioremediation pathways.

Other advantages and characteristics of the present invention will appear in the light of the experimental section and the examples which follow.

In the present disclosure, any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

The following indications are intended to further illustrate certain preferred embodiments of the invention and the mechanism on which the invention relies. They should not be construed as limiting in nature. Those skilled in the art will recognize or be able to ascertain, using not more than routine experimentation, numerous equivalents to the specific substances and procedures described herein. Such equivalents are considered to be within the scope of this invention, and are covered by the following claims.

Other advantages and characteristics of this invention will appear in the light of the detailed description which follows.
Detailed Description of Preferred Embodiments Along with starvation, cold and heat, dehydration or desiccation is one of the most frequent and severe challenges to living cells[9]. Therefore, resistance to desiccation is important part of life's robustness. Bacterium *Deinococcus radiodurans* is the best known extremophile among a handful of organisms found to resist extremely high exposures to ionizing radiation and desiccation[10,11]. It appears that the evolution of *D. radiodurans*' extreme radiation resistance is a by-product of natural selection for its desiccation resistance[12]. Selection for desiccation resistance in bacteria co-selects radiation resistance[13], and all of 41 tested *Deinococcus radiodurans* radiation sensitive mutants are also desiccation sensitive proportionally to their radiation sensitivity[12]. Both treatments have in common that they cause extensive intracellular DNA double strand breakage (DSB)[12] which is the most severe form of genomic damage because a single unrepaired DSB is usually lethal[14]. Standard vegetative prokaryotic and eukaryotic cells can repair less than a dozen simultaneous DSBs[15]. *D. radiodurans* survives ionizing radiation breaking its genome into several hundred fragments (up to 2000 DSBs per cell containing 4 to 10 copies of its genome) due to a DNA repair process accomplishing an efficient and precise fragment assembly[16,10,11] that is a physical equivalent of the computer-assisted contig assembly of shotgun sequenced random genomic fragments.

*D. radiodurans* is a small non-sporulating and non-pathogenic bacterium whose sequenced genome is composed of two circular chromosomes (2.65 and 0.41 mega bp) and two circular plasmids (0.177 and 0.046 mega bp)[17]. Because the recA and polA mutants of *D. radiodurans* are its most radiation sensitive mutants[10,11], the RecA recombinase and DNA Polymerase I (PolA) clearly play key roles in the repair of shattered chromosomal DNA. With few if any exceptions[18], this DNA repair process in *D. radiodurans* is much more efficient than are the RecA and PolA dependent repair processes in other biological species, but its molecular mechanism remained a mystery[19]. Neither the comparative amounts, nor the enzymatic properties of the RecA and PolA proteins gave any clear hint[19,20]. The chromosomal copy number[21] and special forms of chromatin[14,15] have been evoked, but it turns out that neither can account for *D. radiodurans*' resistance[19,20].

This invention reveals and makes use of a new form of DNA repair involving mutually dependent DNA replication and recombination processes, one of which is reminiscent of a single-round multiplex PCR (FIG. 4), reconstituting functional *D. radiodurans* chromosomes shattered by 7 kGy (0.7 megarad) gamma ray radiation to 25-30 kb DNA fragments and causing only about 10% lethality.

Figure 4:
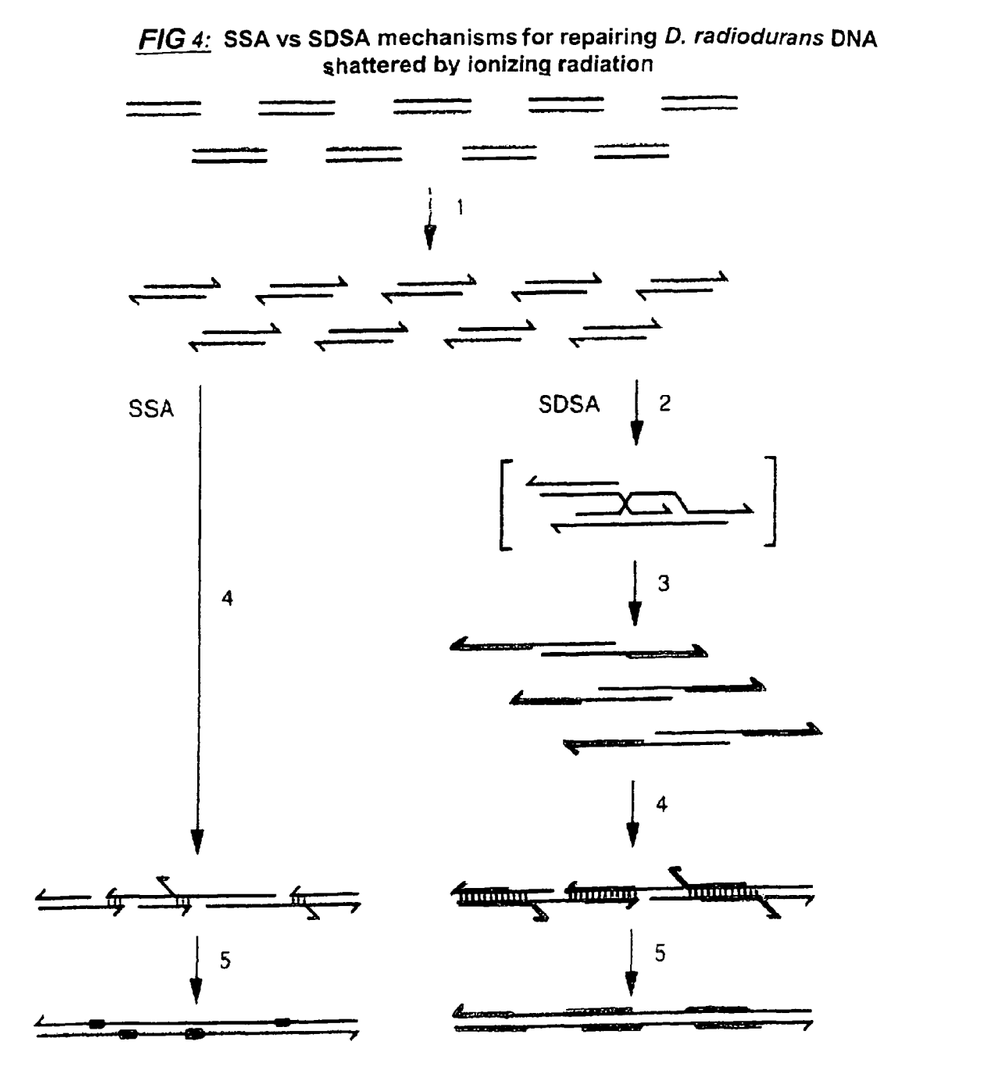

In this respect, the efficiency of UV light in producing DSBs by photolysis of 5-BrdU, suggests that such blocks of newly synthesized double stranded DNA in repaired chromosomes are large, in agreement with density gradient analysis (FIG. 4). The fragmented chromosomes are probably not homologously paired because in such a case (e.g., a yeast meiosis) the SDSA repair synthesis is limited to the short region between recessed ends of the individuals DSBs[4,6]. The structure of chromosomes repaired by ESDSA is shown in FIG. 1. The distinct feature of the ESDSA model is that it involves an "ends-out" multiplex PCR-like step (steps 2 and 3 in FIG. 1) resulting in long newly synthesized single strand overhangs that allow an accurate annealing process. Alternatives to the ESDSA mechanism, e.g., NHEJ or HR working exclusively on newly synthesized DNA ends, are highly unlikely. A SSA mechanism with an extensive nick translation synthesis is conceivable; however the *E. coli* Klenow fragment PolA complements *D. radiodurans* polA mutants for resistance to gamma radiation[22] showing no requirement of nick translation for DNA repair.

Figure 2:
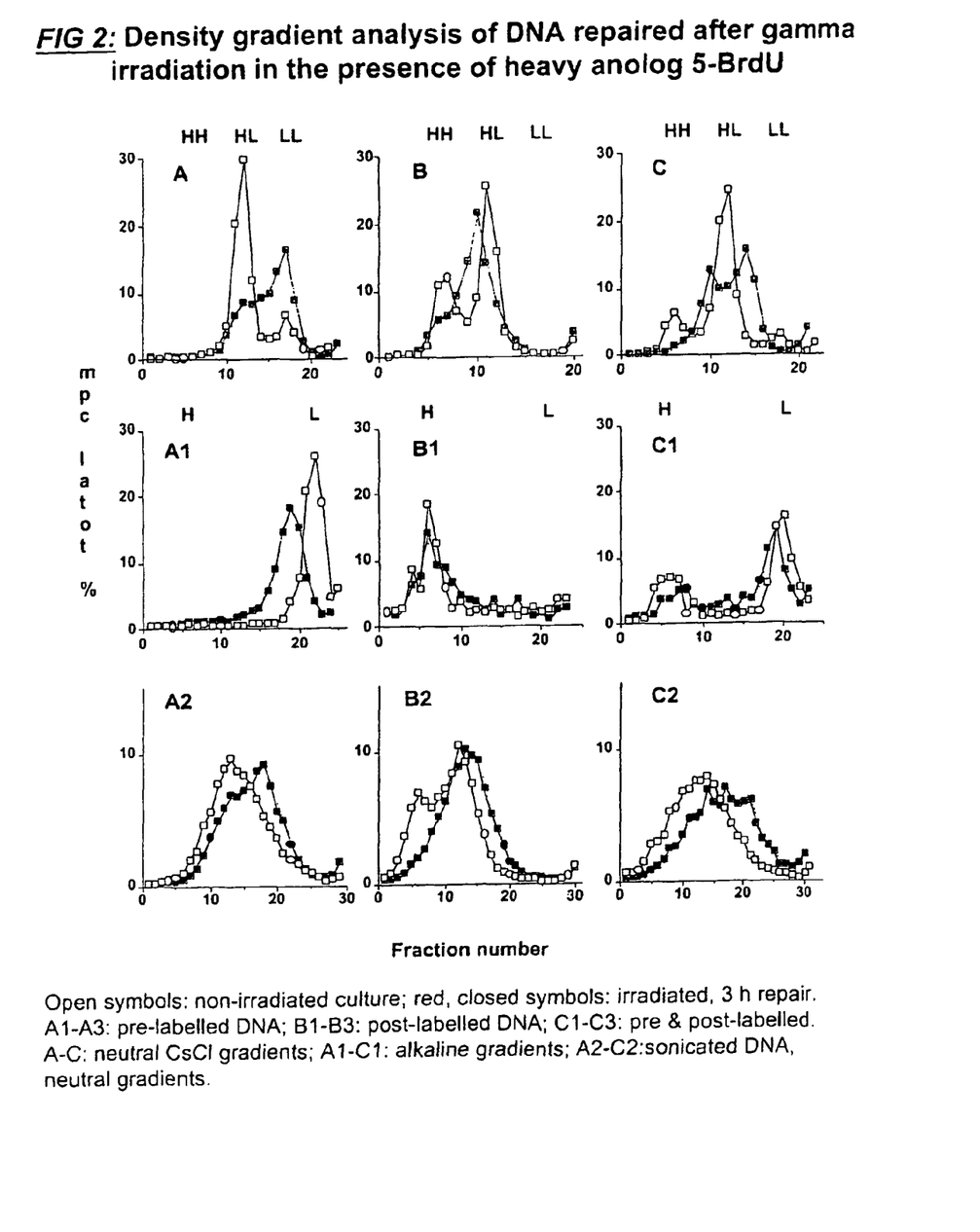
Figure 3:
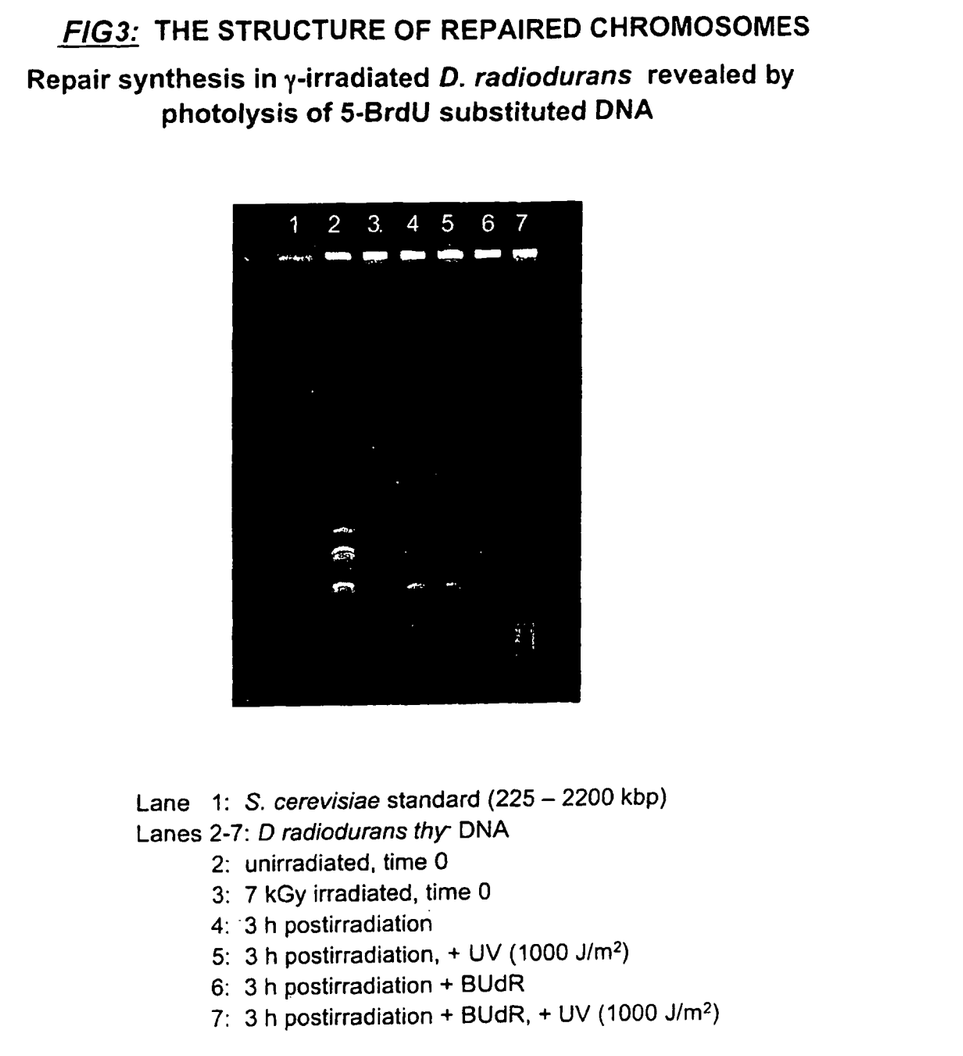
FIG. 3 is a representation of a photolysis of *D. radiodurans* DNA shattered by ionizing radiation and repaired in the presence of 5-BrdU. PFGE patterns of Not1 fragments of *D. radiodurans* DNA (2-7) and the molecular weight standards of *S. cerevisiae* chromosomes (1). DNA from: (2) non-irradiated cells; (3) cells irradiated with 7 kGy gamma radiation and incubated for 3 h in standard medium before (5) and after (6) exposure to 1000 J/m2 UV light; (6) irradiated cells repaired in 5-BrdU containing medium before (6) and after (7) exposure to 1000 J/m2 UV light.

The pattern of DNA repair seen in PFGE (FIG. 2E) and in optical mapping experiments[23] suggests that the majority of DNA fragments "grow" progressively and that most fragments are being used early in the chromosomal assembly process (FIG. 2). One can therefore envisage ESDSA "chain reactions" involving numerous "nucleation" points in the cell producing long linear DNA repair intermediates. Such long linear DNA, if shorter than the chromosome size, would not be likely to find the exact two-end matching chromosomal segment to complete the circular chromosome structure by ESDSA or SSA. Such shorter-than-chromosome linear intermediates, as well as those longer than chromosome size, would require homologous, typically RecA-dependent, recombination[24] to produce mature unit circular chromosomes (FIG. 3). This is consistent with PFGE experiments with a recA mutant (FIG. 2E). Both DNA synthesis and repair are less efficient in the recA mutant (FIG. 2E,F) than in wild type, so that it is therefore possible that deinococcal RecA, through its preferential double-strand binding activity[20] brings together DNA fragments with overlapping homology that should facilitate an ESDSA mechanism. However, the key involvement of RecA occurs late in the repair process (FIG. 3).

PolA, but not recA, mutant is clearly deficient in ESDSA repair (FIG. 2). However, DNA base and sugar damage by radiation-induced oxygen free radicals, which can cause single-strand breaks directly and, more frequently, by proximal base excision repair (BER) events, are at least 10 times more frequent than DSBs[25] and typically require PolA for the completion of repair[26]. Therefore, it is expected that PolA protects the integrity of the DNA fragments (see the loss of fragments in FIG. 2C) produced by gamma radiation by repairing single nucleotide gaps created by the BER enzymes, a prerequisite for their assembly where PolA is presumably directly involved in the ESDSA process (FIG. 1). However, before the isolation of a conditional mutant of DNA polymerase III, one cannot exclude the possibility that PolA only initiates a DNA polymerase III-catalyzed single strand elongation or even contributes only to the maintenance of fragments.

Unlike other bacteria, all radiation resistant bacterial species show condensed nucleoids even after ionizing radiation[27]. It was suggested that a special ring-like chromatin holds broken DNA ends in register and facilitates repair by NHEJ[3]. However, the high concentration of DNA fragments in the condensed nucleoid is expected to facilitate any bimolecular homologous interaction required for DNA repair, e.g., in SDSA/ESDSA, SSA and HR. Perhaps, in addition to the peculiarity of the RecA[20], the condensed chromatin is another evolutionary innovation of *D. radiodurans* assuring high efficiency of ESDSA and, therefore, radiation resistance.

As to the question whether ESDSA can account for the apparent fidelity of DNA repair in *D. radiodurans*, one can generally say that the larger the number of DNA fragments, the higher the precision required for avoiding their incorrect assembly and the longer must be the required homology. If there are unusually many DSBs, unusually long homology—and hence single strand exposure—is required. Such unusually long overhangs are newly synthesized in the course of the ESDSA (FIG. 1). However, any homology-based repair of shattered DNA raises the question of the accuracy of assembly of chromosomal fragments containing repetitive sequences. The fact that all long repeats, e.g., transposons, have been completely counter-selected from *D. radiodurans* genome[17,28] may be due to their deleterious effect on the precision of the ESDSA. The problem of an incorrect fragment assembly via repetitive sequences could be circumvented in ESDSA if the single-stranded overhangs were much longer than the longest repetitive sequences. In that case, annealing only a repeated sequence block within a long single-stranded overhang could not readily link the two fragments. Such partially annealed structures are the preferred substrates for DNA helicases and, therefore, these aberrant DNA associations should be readily aborted. The avoidance of lethal non-contiguous DNA fragment assembly may have provided sufficient selective pressure for the evolution of the ESDSA mechanism (with long single stranded overhangs) rather than a SSA (with shorter overhangs) (FIG. 1). The inventors' experiments suggest that the size of ESDSA overhangs is similar to the fragment size, i.e., about 20 to 30 kb—much longer that the longest *D. radiodurans*' repetitive sequences (IS of about 1 kb)[17,28].

As the precision of fragment assembly on the ESDSA process becomes high due to long overhangs, the fidelity of making such overhangs by strand extension (the bracketed intermediates in FIG. 1) becomes limiting for the global fidelity DNA repair. It is therefore suggested by the inventors that one can think of four strategies for assuring the fidelity of both priming and annealing:

(1) homologous pairing of double-stranded DNA fragments before initiation of D-loops, perhaps by the deinococcal RecA[20], (2) editing the pairing process by mismatch repair[29,30], (3) repeat-binding proteins[17] preventing sequence repeats from becoming single-stranded or from annealing, and (4) stable secondary structures (in practice hairpins) of repetitive sequences[28] preventing their annealing.

Provided that one could learn what are the intermediate steps in deinococcal DNA repair, then reproducing, in silico, the fragment assembly process could become an alternative to the current contig programs. Finally, given the high transformability of *D. radiodurans* by exogenous DNA as shown according to this invention, it may be that, in the evolutionary past of *D. radiodurans*, an ESDSA-like repair after desiccation periods has led to the incorporation of foreign DNA. This would account for the extraordinary diversity of genetic lineages represented in the *D. radiodurans* chromosome (*Bacillus, Thermus* and multiple eukaryotic genes)[17,28].

The experiments on which the present invention is based are summarized as follows.

DNA Synthesis and Repair of *D. Radiodurans* Chromosomes Shattered by Radiation.

To discriminate between these hypothetical mechanisms, we explored in parallel the kinetics of the joining of DNA fragments by pulsed-field gel electrophoresis (PFGE) and the rate of DNA synthesis by 15 min 3H-TdR pulse labelling following 7 kGy gamma radiation.

There is clearly a temporal coincidence of the fragment assembly and the observed massive DNA synthesis occurring without cell division at much higher rate than in the growing non-irradiated cell culture (FIGS. 1A and B). This DNA synthesis is absent in a polA strain (FIG. 1D) that also shows no evidence of DNA repair (FIG. 1C). Along with high radiation sensitivity of the polA mutant, these observations cannot be easily accommodated by mechanisms (i) and (ii). They generally agree with all mechanisms (iii-v) involving extensive DNA synthesis. SDSA (iv), and to a lesser degree SSA (iii) mechanisms are favored if the PolA dependence is due to PolA (with or without participation of DNA pol III) catalyzed single-strand elongation (FIG. 4), but the CC mechanism (v) cannot be a priori excluded because PolA could initiate or otherwise facilitate a Pol III-catalyzed semi-conservative two-strand synthesis (replication forks).

Figure 5:
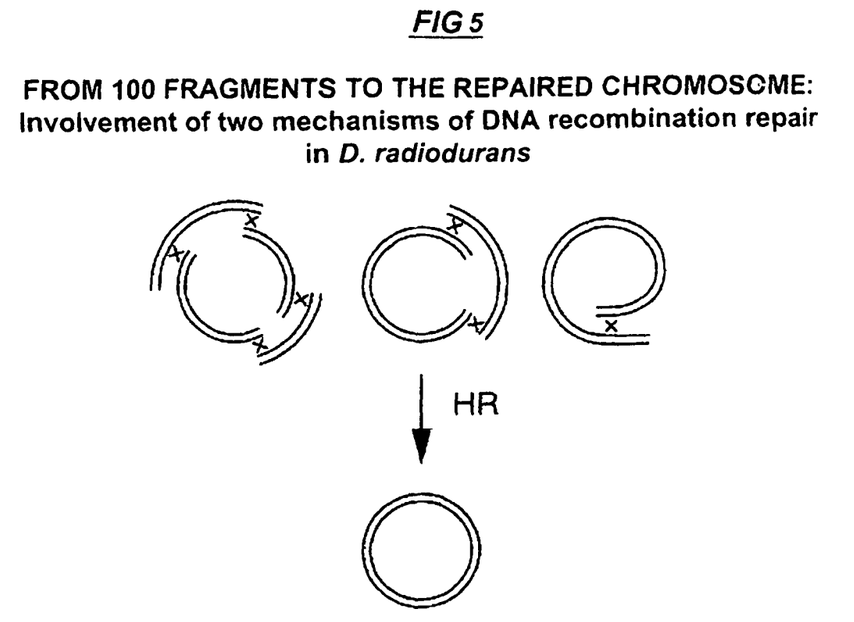
FIG. 5 shows a model for the maturation of circular chromosomes by homologous recombination. Whereas RecA-independent ESDSA (FIGS. 1 and 4) can produce long linear intermediates, closing the structure of the *D. radiodurans* genome (consisting of four circular elements) by ESDSA is highly unlikely. To mature into the unit size circular chromosomes, the overlapping long linear fragments—or linear intermediates longer than chromosome—require crossovers (X) via homologous recombination (HR). This step requires RecA (FIG. 1,5).

We confirm the already observed[5] largely RecA-independent fragment assembly (FIG. 1E) which is paralleled by a substantial DNA synthesis during the time of effective repair (FIG. 1F). These experiments establish a correlation between the PolA-dependent DNA synthesis and the recombination repair of highly fragmented *D. radiodurans* chromosomes. The strict requirement of the RecA for the appearance of full-size chromosomes, a prerequisite for cell survival, suggests RecA's key involvement in the maturation of functional circular chromosomes (FIG. 5).

Density Gradient Analysis of the Structure of Repaired Chromosomes

The density analysis of DNA from unirradiated *D. radiodurans* cultures (FIG. 2C) agrees with the Meselson-Stahl experiment with *E. coli*, i.e., the replication of all chromosomal elements appears semi-conservative: the H/L (heavy/light) density appears after the first replication cycle, H/H during the second. Furthermore, upon DNA denaturation and centrifugation in alkaline CsCl gradients, all single-stranded material segregates into either H or L densities (FIGS. 2A1, B1, C1). Because of the pattern of radioactive (L 3H-TdR)* (* denotes radioactive label) and density (H 5-BrdU) labelling, the non-irradiated growing *D. radiodurans* cultures show, in the pre-labelling regime, only H/L* (FIG. 2A) (and only L* in denaturing gradients, FIG. 2A1) material; in the post-labelling predominantly the H*/L and—to the extent of second replication round—also the H*/H* (FIG. 2B) (and only *H in denaturing gradients, FIG. 2B1). We shall call "old" the light DNA synthesized before irradiation and "new" the heavy DNA synthesized after irradiation.

Because only old DNA is damaged in radiation experiments, and the repair takes place in the heavy medium, the two strands of the DNA repaired by NHEJ and HR are expected to be essentially old/old and those made by CC fully new/new. The density patterns of DNA repaired during 3 hours after gamma radiation do not resemble semi-conservative replication and do not support either NHEJ, HR or CC as the predominant repair mechanism (text above and FIGS. 2A-C). In neutral density gradients, the old "pre-labeled" DNA is spread towards intermediate densities by the 5-BrdU incorporation after irradiation (FIG. 2A). On the other hand, the "post-labeled" new DNA synthesized after irradiation is shifted towards heavy densities (FIG. 2B). Both results are compatible with the SDSA (and, to a lesser degree, SSA) mechanism but only if, after denaturation, single strands also show intermediate densities because of the expected patchwork of the blocks of old and new material (FIG. 4). Indeed, in alkaline CsCl density gradients, the densities of pre-labeled single strands are shifted substantially from light (old) towards heavy (new) (FIG. 2C1). Because the size of the DNA isolated by the method described is in the range of 15 to 20 kb, i.e., generally smaller than the in vivo size of fragments following 7 kGy irradiation (about 30 kb), the detection of fragments containing old and new material is diminished. These results support the hypothesized "distributive" mode[31] of DNA (repair) replication predicted by SDSA and, to a lesser degree, SSA mechanism.

What is the relative size of newly synthesized patches? FIG. 2A1 shows that, in the "pre-labelling" regime, the density of the majority of single stranded material is heavier than light (old) but lighter than heavy (new). The reciprocal is not true: in the "post-labelling" regime, the single-stranded DNA is under the heavy peak and skewed towards lighter densities (FIG. 2B1). In other words, during the repair in the presence of 5-BrdU of initially light fragments, the old light strands are made heavier (by association with heavy material) than are the new heavy strands made lighter (by association with light material). This suggests that, in the analyzed DNA fragments, the tract of newly synthesized (density and radioactively labeled) material is often longer than the tract of original light (radioactively but not density labeled) material. This agrees well with the SDSA model. If the SSA model were correct, it would require that the recession of fragment ends be very extensive to explain the massive PolA-dependent DNA synthesis associated with repair (FIG. 1A,B). On the single strand level, the repaired DNA appears as a patchwork of old and new material, expected from both SDSA and SSA) mechanisms (FIG. 4).

If one mechanism is predominant, can we discriminate between the two? SSA mechanism predicts that—upon DNA breakage by sonication (to about 3 kb fragments, not shown)—the double-stranded DNA should be segregating towards the new/old and old/old, whereas the SDSA mechanism predicts (in the post-labelling regime) a significant segregation towards the new/new densities in neutral gradients (see FIG. 4). FIGS. 2 A2-C2 show a very large density distribution of sonicated DNA fragments obscuring the detection of any minority distinct density molecular species.

The amount of L/L material in the pre-labelling experiment (FIG. 2A) shows that a large fraction of molecules contains no significant tract of DNA repair synthesis. Because the size of isolated DNA is even smaller than the fragment size of radiation-broken DNA, it could be that the L/L material represents (a) DNA fragments dissociated from repair synthesis, (b) the unrepaired DNA fragments from dead cells and/or (c) the unused fragments from surviving cells. Given that we see no evidence of unused DNA fragments in PFGE experiments (FIG. 1A,E), option (a) remains most likely.

Distribution of Newly Synthesized DNA Patches Revealed by DNA Photolysis

5-BrdU substitution sensitizes DNA strands to breakage by photolysis using UV or short wavelength visible light[32-34]. We confirm that, also under our experimental conditions, one-strand 5-BrdU substitution (during 1.5 h, i.e., less than one generation time) of non-irradiated *D. radiodurans* chromosomes does not significantly sensitize DNA to the double-strand breakage by the UV induced photolysis. Two-strand 5-BrdU substitution causes extensive DNA breakdown (results not shown). The intracellular photolysis decomposes DNA repaired in 5-BrdU by double-strand breakage almost reproducing the pattern of the initial DNA breakage by gamma rays seen before the onset of repair (FIG. 3). UV light induced DNA fragmentation does not increase beyond the saturating dose of 250-500 J/m$^2$, whereas it does for the fully substituted DNA (not shown). This pattern of 5-BrdU-dependent photolysis suggests that most, perhaps all, reassembled fragments are linked together via double-stranded blocks of newly synthesized DNA (red colored in FIG. 4) as predicted by the SDSA.

Materials and Methods

Bacterial strains, growth conditions, and gamma irradiation. The following *D. radiodurans* strains were used: R1 (ATCC 13939) wild type[35], GY10922 D(cinA-recA)1::kan[36], and IRS501 polA (J. R. Battista). A thymine-requiring (thy-) derivative of R1 strain was isolated by selection on solid minimal medium containing thymine (50 mg/ml) and trimethoprim (100 mg/ml)[37].

Bacteria were grown in TGY broth (0.5% tryptone, 0.1% glucose, 0.15% yeast extract) at 30° C. to the late exponential phase (OD650=0.6-0.8). Cultures were washed in 10 mM sodium phosphate buffer, concentrated 10 times in the same buffer, and irradiated on ice with a 60Co gamma ray source at a dose rate of 11 Gy/s. The dose of 7 kGy was applied to the cells in all irradiation experiments. The number of viable cells was estimated by plating serial dilutions onto TGY plates. The plates were incubated for 34 days at 30° C. before the colonies were counted.

Kinetics of DNA repair measured by pulsed-field gel electrophoresis. Irradiated cultures were diluted in TGY to an OD650=0.2 and incubated at 30° C. At intervals during post-irradiation incubation, 5-ml samples were taken to prepare DNA plugs as described by Mattimore and Battista4. The DNA contained in the plugs was digested with 60 units of NotI restriction enzyme (Roche) for 16 h at 37° C. After digestion, the plugs were subjected to pulsed-field gel electrophoresis in 0.5×TBE using a CHEF-DR III electrophoresis system (Bio-Rad) at 6 V/cm2 for 20 h at 14° C., with a linear pulse ramp of 50-90 s and a switching angle of 120°.

Rate of DNA synthesis measured by DNA pulse labelling. At intervals during exponential growth of both non-irradiated and irradiated cultures, 0.5 ml samples were taken and mixed with 0.1 ml pre-warmed TGY medium containing 6 mCi 3H-thymidine (Amersham; specific activity 86 Ci/mmol). Pulses were terminated after 15 min by addition of 2 ml ice-cold 10% TCA. Samples were kept on ice for at least 1 h, and then collected by suction onto Whatman GF/C filters followed by washing with 5% TCA and 96% ethanol. Filters were dried overnight at room temperature, and placed in 5 ml scintillation liquid. The precipitated counts were measured in a liquid scintillation counter (Wallac).

Radioactive and density DNA labelling. *D. radiodurans* thy-cells were radioactively and density labeled during growth in the presence of 3H-thymidine and 5-bromo-2'-deoxyuridine (5-BrdU), respectively. Density labelling was performed in all experiments by adding 5-BrdU to the medium only after irradiation. The radioactive labelling was performed in three different regimes. (a) "Pre-labelling": cells were grown overnight in TGY supplemented with 5 mCi/ml 3H-thymidine. They were collected by centrifugation, washed twice with phosphate buffer, concentrated 10 times in the same buffer, and exposed to 7 kGy gamma radiation. Both irradiated and non-irradiated cultures were diluted to an OD650=0.2 in TGY containing 20 mg/ml 5-BrdU. The non-irradiated culture was grown in 5-BrdU-supplemented TGY for 2.5 h (corresponding to one mass-doubling), while the irradiated culture was grown for 3 h (the time required for DSB repair to be completed) at 30° C. (b) "Post-labelling": cells were grown overnight in non-radioactive TGY, and radioactivity (20 mCi/ml 3H-thymidine) was added to the 5-BrdU-supplemented TGY only after irradiation. The experimental procedure was otherwise the same as described for "pre-labelling". (c) "Pre- and post-labelling": the procedure was a combination of (a) and (b), i.e. the cells were radioactively labeled before and after irradiation.

DNA preparation and density gradient analysis. Radioactively and density labeled DNA was isolated from *D. radiodurans* by the use of Qiagen DNeasy Tissue Kit according to the supplier's instructions. In some experiments, the DNA was additionally fragmented by sonication. For that purpose, 100-ml DNA samples were subjected to sonication (Vibracell 72434, Bioblock) with increasing number of 5 sec bursts. Optimal sonication conditions producing 3-5 kb fragments were determined by gel electrophoresis.

The DNA was centrifuged to equilibrium in neutral or alkaline cesium chloride (CsCl) solution (1.7246 g/ml) in a VTi90 rotor (Beckman) for 24 h at 40.000 rpm and 20° C. To obtain the desired CsCl concentration, the refractive index of CsCl solution was adjusted (by adding water) to 1.4030 for neutral gradients, and to 1.4050 for alkaline gradients. For alkaline gradients, the DNA was denatured by 10 min heating in boiling water, chilling in ice water, and the CsCl solution was adjusted to pH 11.8. Gradients were collected from the bottom of pierced tubes (OptiSeal 4.9 ml, Beckman) in about 25 (12-drop) fractions. 100-ml aliquots of fractions were applied on round filters, dried under the lamp for several hours, and the radioactivity was measured by scintillation counter.

UV-induced photolysis of BU-substituted DNA. *D. radiodurans* thy-culture was grown and irradiated with 7 kGy gamma radiation as described above. The irradiated culture was diluted to an OD650=0.2 and grown in 5-BrdU-supplemented TGY for 3 h. The cells were collected by centrifugation, resuspended in the phosphate buffer and incubated (starved) in buffer for one hour at 30° C. Cell suspension was cooled in ice and exposed in thin layer to 1000 J/m2 of 254-nm UV light. Both UV-irradiated and non-irradiated cells were embedded in agarose plugs for DNA analysis by PFGE (see above).

References

1 Lees-Miller, S. P. & Meek, K. Repair of DNA double strand breaks by non-homologous end joining. *Biochimie* 85, 1161-1173 (2003).

2 Wilson, T. E., Topper, L. M. & Palbos, P. L. Non-homologous end-joining: bacteria join the chromosome breakdance. *Trends Biochem. Sci.* 28, 62-66 (2003).

3 Levin-Zaidman S. et al. Ringlike structure of the *Deinococcus radiodurans* genome: a key to radioresistance? *Science* 299, 254-256 (2003).

4 Haber, J. E. Partners and pathways repairing a double-strand break. *Trends Genet.* 16, 259-264 (2000).

5 Daly, M. J. & Minton, K. W. An alternative pathway of recombination of chromosomal fragments precedes recA-dependent recombination in the radioresistant bacterium *Deinococcus radiodurans*. *J. Bacteriol.* 178, 4461-4471 (1996).

6 Paques, F. & Haber, J. E. Multiple pathways of recombination induced by double-strand breaks in *Saccharomyces cerevisiae*. *Microbiol. Mol. Biol. Rev.* 63, 349-404 (1999).

7 Gloor, G. B., Targeted gene replacement in *Drosophila* via P element-induced gap repair. *Science* 253, 1110-1117 (1991).

8 Lederberg, J. Recombination mechanisms in bacteria. *J. Cell Comp. Physiol.* 45, 75-107 (1955).

9 Potts, M. Desiccation tolerance: a simple process? *Trends Microbiol.* 9, 553-559 (2001).

10 Minton, K. W. DNA repair in the extremely radioresistant bacterium *Deinococcus radiodurans*. *Mol. Microbiol.* 13, 9-15 (1994).

11 Battista, J. R., Earl, A. M. & Park, M. J. Why is *Deinococcus radiodurans* so resistant to ionizing radiation? *Trends Microbiol.* 7, 362-365 (1999).

12 Mattimore, V. & Battista, J. R. Radioresistance of *Deinococcus radiodurans* functions necessary to survive ionizing radiation are also necessary to survive prolonged desiccation. *J. Bacteriol.* 178, 633-637 (1996).

13 Sanders, S. W. & Mawcy, R. B. Isolation of radiation-resistant bacteria without exposure to radiation. *Appl. Environ. Microbiol.* 38, 436-439 (1979).

14 Krasin, F. & Hutchinson, F. Repair of DNA double-strand breaks in *Escherichia coli* which requires recA function and the presence of duplicate genome. *J. Mol. Biol.* 116, 81-98 (1977).

15 Fujimori, A. et al., Rad52 partially substitutes for Rad51 paralog XRCC3 in maintaining chromosomal integrity in vertebrate cells. *EMBO J.* 20, 5513-5520 (2001).

16 Dean, C. J., Feldschreiber, P. & Lett, J. T. Repair of X-ray damage to the deoxyribonucleic acid in *Micrococcus radiodurans*. *Nature* 209, 49-52 (1966).

17 White, O. et al. Genome sequence of the radioresistant bacterium *Deinococcus radiodurans*. *Science* 286, 1571-1577 (1999).

18 Ferreira, A. C. et al. Characterization and radiation resistance of new isolates of *Rubrobacter radiotolerans* and *Rubrobacter xylanophilus*. *Extremophiles* 3, 235-238 (1999).

19 Narumi, I. Unlocking radiation resistance mechanisms: still a long way to go. *Trends Microbiol.* 11, 422-425 (2003).

20 Cox, M. M. & Battista, J. R. Resisting ionizing radiation: *Deinococcus radiodurans* is a little different (not that there's anything wrong with that). *Nature Microbiology in press*.

21 Harsojo, Kitayama, S. & Matsuyama, A. Genome multiplicity and radiation resistance in *Micrococcus radiodurans*. *J. Biochem.* (Tokyo) 90, 877-880 (1981).

22. Gutman, P. D., Fuchs, P. & Minton, K. W. Restoration of the DNA damage resistance in *Deinococcus radiodurans* DNA polymerase I mutants by *Escherichia coli* DNA polymerase I and Klenow fragment, *Mutation Research, DNA repair* 314, 87-97 (1994).

23 Lin, J. et. al. Whole-genome shotgun optical mapping of *Deinococcus radiodurans*. *Science* 285, 1558-1562 (1999).

24 Radding, C. M. Homologous pairing and strand exchange in genetic recombination. *Annu Rev Genet* 16, 405-437 (1982).

25 Harris, D. R. et al. Preserving genome integrity: the DdrA protein of *Deinococcus radiodurans* R1. *PLoS Biol.* 2, e304 (2004).

26 Lindahl, T. DNA repair enzymes. *Annu Rev Biochem.* 51, 61-87 (1982).

27 Zimmerman, J. M. & Battista, J. R. A ring-like nucleoid is not necessary for radioresistance in *Deinococcaceae*. *BMC Microbiol.* 5, 17-27 (2005).

28 Makarova, K. S. et al. Genome of the extremely radiation-resistant bacterium *Deinococcus radiodurans* viewed from the perspective of comparative genomics. *Microbiol. Mol. Biol. Rev.* 65, 44-79 (2001).

29 Rayssiguier, C., Thaler, D. S. & Radman, M. The barrier to recombination between *Escherichia coli* and *Salmonella typhimurium* is disrupted in mismatch-repair mutants. *Nature* 342, 396-401 (1989).

30 Mennecier, S., Coste, G., Servant, P., Bailone, A. & Sommer, S. Mismatch repair ensures fidelity of replication and recombination in the radioresistant organism *Deinococcus radiodurans*. *Mol. Genet. Genomics* 272, 460-469 (2004).

31 Meselson, M. & Stahl, F. W. The replication of DNA. *Cold Spring Harb. Symp. Quant. Biol.* 23, 9-12 (1958).

32 Lion, M. B. Search for a mechanism for the increased sensitivity of 5-bromouracil-substituted DNA to ultraviolet radiation. II. Single-strand breaks in the DNA of irradiated 5-bromouracil-substituted T3 coliphage. *Biochim. Biophys. Acta* 209, 24-33 (1970).

33 Radman, M., Roller, A. & Errera, M. Protection and host cell repair of irradiated bacteriophage lambda: III Ultraviolet irradiation of 5-bromouracil-substituted phage. *Mol. Gen. Genet.* 104, 152-156 (1969).

34 Lohman, P. H. M., Bootsma, D. & Hey, A. H. The influence of 5-bromodeoxyuridine on the induction of breaks in deoxyribonucleic acid of cultivated human cells by X-irradiation and ultraviolet light. *Radiation Res.* 52, 627-641 (1972).

35 Anderson, A. W., Nordon, H. C., Cain, R. F., Parrish, G. & Duggan, D. Studies on a radio-resistant micrococcus. I. Isolation, morphology, cultural characteristics and resistance to gamma radiation. *Food. Technol.* 10, 575-578 (1956).

36 Bonacossa de Almeida, C., Coste, G., Sommer, S. & Bailone, A. Quantification of RecA protein in *Deinococcus radiodurans* reveals involvement of RecA, but not LexA, in its regulation. *Mol. Genet. Genomics* 268, 28-41 (2002).

37 Little, J. G. & Hanawalt, P. C. Thymineless death and ultraviolet sensitivity in *Micrococcus radiodurans*. *J. Bacteriol.* 113, 233-240 (1973).

The invention claimed is:

1. A process for chromosomal engineering, which comprises the steps of:
   1) providing a bacterium having a DNA repair mechanism, for reassembling its fragmented DNA following a radiation and/or desiccation and/or chemical treatment, said mechanism comprising a step of extended synthesis dependent strand annealing (ESDSA) and a step of RecA dependent homologous recombination;
   2) inducing the DNA repair mechanism by submitting the bacterium to radiation, desiccation and/or chemical treatment liable to damage the DNA, so as to substantially shatter its chromosomes into short fragments, said DNA repair mechanism comprising: annealing complementary single strand tails extended by an extended synthesis dependent strand annealing (ESDSA) templated on partially overlapping DNA fragments of said shattered chromosomes; and converting the resulting long linear DNA intermediates into intact circular chromosomes, by a RecA dependent homologous recombination;

3) inserting into the shattered chromosomes at least one foreign natural DNA or foreign synthetic DNA so as to become an integral part thereof during the process of DNA repair of step 2); and 4) optionally separating and collecting the recombined chromosomes thus obtained, wherein the process is carried out in a bacterium of the *Deinococcus* genus.

2. The process of claim 1, wherein the bacterium having a DNA repair mechanism is exposed to at least one gamma irradiation of about 0.7 megarad (7 kGy) or to desiccation.

3. The process of claim 1, wherein the foreign DNA comprises entire operons encoding biosynthetic pathways.

4. The process of claim 1, wherein the foreign DNA comprises synthetic 3' extension.

5. The process of claim 1, wherein, to promote successful integration in the bacterial chromosome, the foreign DNA is extended by synthesis or end-addition by DNA ligase with a bacterial sequence corresponding to an IS sequence.

6. The process of claim 5, wherein all of the foreign DNA are extended by the same sequence.

7. The process of claim 1, which comprises the use of a natural transformation capacity of bacteria, bacterial sex, or an artificial process for introducing foreign DNA into the bacterium having a DNA repair mechanism undergoing DNA repair.

8. The process of claim 7, wherein the DNA repair mechanism is induced by ionizing or ultraviolet irradiation, or by chemicals that damage DNA, before or after the introduction of foreign DNA into the said bacterium having a DNA repair mechanism.

9. A method for producing libraries of inter-species recombined chromosomes encoding metabolic pathways, which comprises a step of preparing recombined chromosomes according to the process of claim 1 to be used for producing said libraries.

10. The method of claim 1, which is carried out in *Deinococcus radiodurans*.

11. A process for chromosomal engineering, which comprises the steps of:

1) providing a *Deinococcus* bacterium having a DNA repair mechanism for reassembling its fragmented DNA following a radiation and/or desiccation and/or chemical treatment;

2) submitting the bacterium to radiation, desiccation and/or chemical treatment liable to damage the DNA, so as to substantially shatter its chromosomes into short fragments and to induce the DNA repair mechanism;

3) adding to the shattered chromosomes at least one foreign natural DNA or foreign synthetic DNA so as to become an integral part thereof during the process of DNA repair of step 2); and 4) optionally separating and collecting the recombined chromosomes thus obtained.

* * * * *